United States Patent
Prod'hom et al.

(10) Patent No.: US 9,242,038 B2
(45) Date of Patent: Jan. 26, 2016

(54) DIABETES THERAPY DEVICE ENABLING SHIFTING OF PARAMETER PROFILES

(75) Inventors: Gilles Prod'hom, Bern (CH); Thierry Prud'homme, Hergiswil (CH); Robert Hellwig, Bern (CH); Bernhard Teupe, Bad Mergentheim (DE)

(73) Assignee: Roche Diagnostics International AG, Steinhausen (CH)

( * ) Notice: Subject to any disclaimer, the term of this patent is extended or adjusted under 35 U.S.C. 154(b) by 331 days.

(21) Appl. No.: 12/888,746

(22) Filed: Sep. 23, 2010

(65) Prior Publication Data

US 2011/0238033 A1     Sep. 29, 2011

(30) Foreign Application Priority Data

Sep. 25, 2009   (EP) .................................... 09012182

(51) Int. Cl.
 *A61M 5/42*     (2006.01)
 *A61M 5/142*    (2006.01)
 (Continued)

(52) U.S. Cl.
 CPC ......... *A61M 5/14244* (2013.01); *A61M 5/1723* (2013.01); *G06F 19/3468* (2013.01); *A61M 2005/14208* (2013.01); *A61M 2205/50* (2013.01); *A61M 2205/52* (2013.01)

(58) Field of Classification Search
 CPC ............... A61M 2005/1726; A61M 5/1723; A61M 5/172; A61M 5/16836; A61M 5/14244; A61M 2230/201; A61M 2005/14268; A61B 5/14532; A61B 5/1495; G06F 19/3418; G06Q 50/24
 USPC ..................................... 604/500, 66–67, 131
 See application file for complete search history.

(56) References Cited

U.S. PATENT DOCUMENTS

| | | | | |
|---|---|---|---|---|
| 4,494,950 A | * | 1/1985 | Fischell | A61B 5/0002 128/903 |
| 6,923,784 B2 | * | 8/2005 | Stein | A61M 5/14276 604/65 |

(Continued)

FOREIGN PATENT DOCUMENTS

| | | |
|---|---|---|
| EP | 2 108 393 A1 | 10/2009 |
| WO | 03/053498 A2 | 7/2003 |
| WO | 2006/066926 A1 | 6/2006 |

OTHER PUBLICATIONS

"Diabetes Mellitus and Heart Failure: Epidemiology, Mechanisms, and Pharmacotherapy", The American Journal of Cardiology, p. 119B by Masoudi.*

(Continued)

*Primary Examiner* — Kami A Bosworth
*Assistant Examiner* — Matthew A Engel
(74) *Attorney, Agent, or Firm* — Dinsmore & Shohl LLP

(57) ABSTRACT

A diabetes therapy device is disclosed herein, which includes a profile memory storing a parameter profile and a dedicated reference time mark. The parameter profile defines at least one parameter that is associated with insulin administration as a function of time for a generally circadian chronobiological cycle. The reference time mark indicates the beginning of the circadian chronobiological cycle and initializes a running time. Insulin amounts to be administered are determined as a function of the running time in accordance with a current matching of the parameter profile. A modified matching based on the reference time mark and an upcoming trigger time is computed and is time-shifted from the current matching, wherein the modified matching is applied by making the modified matching the current matching, such that future insulin amounts to be administered are determined in accordance with the modified matching.

16 Claims, 8 Drawing Sheets

(51) Int. Cl.
*A61M 5/172* (2006.01)
*G06F 19/00* (2011.01)

(56) References Cited

U.S. PATENT DOCUMENTS

| | | | | |
|---|---|---|---|---|
| 6,936,029 | B2* | 8/2005 | Mann | A61M 5/14244 604/131 |
| 8,156,070 | B2* | 4/2012 | Buck | A61M 5/14244 706/62 |
| 9,000,929 | B2* | 4/2015 | Hayter | A61B 5/0002 340/539.1 |
| 2007/0142822 | A1 | 6/2007 | Remde | |
| 2007/0175827 | A1* | 8/2007 | Wariar | A61M 1/1613 210/645 |
| 2008/0106431 | A1 | 5/2008 | Blomquist | |
| 2008/0125701 | A1* | 5/2008 | Moberg | A61B 5/1118 604/67 |
| 2008/0172031 | A1* | 7/2008 | Blomquist | G06F 19/3468 604/500 |
| 2008/0183060 | A1* | 7/2008 | Steil | A61B 5/14865 600/365 |
| 2009/0069745 | A1* | 3/2009 | Estes | A61M 5/14244 604/67 |
| 2009/0163793 | A1* | 6/2009 | Koehler | A61B 5/0002 600/365 |
| 2009/0177147 | A1* | 7/2009 | Blomquist | A61M 5/14244 604/67 |
| 2009/0321277 | A1* | 12/2009 | Heller | G01N 27/3271 205/778 |
| 2010/0228186 | A1* | 9/2010 | Estes | A61M 5/14244 604/66 |
| 2011/0238033 | A1* | 9/2011 | Prod'hom | A61M 5/14244 604/500 |
| 2012/0035431 | A1* | 2/2012 | Sun | A61B 5/0478 600/300 |
| 2012/0302942 | A1* | 11/2012 | DiPierro | A61K 31/135 604/23 |

OTHER PUBLICATIONS

"Effect of sleep on gastroesophageal physiology and airway protective mechanisms", The American Journal of Medicine, vol. 115, Issue 3, p. 114, Aug. 2003 by Pasricha.*
European Search Report, Feb. 19, 2010 for European Application No. EP 09012182.3-1225, pp. 1-8.

* cited by examiner

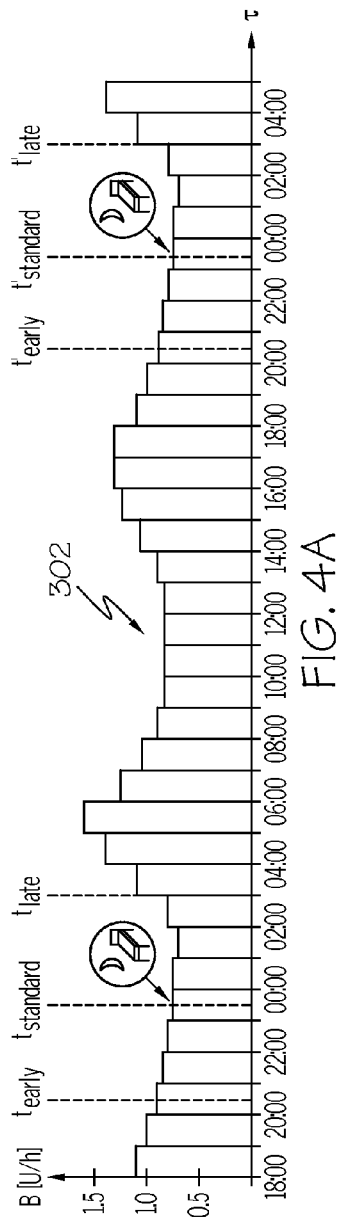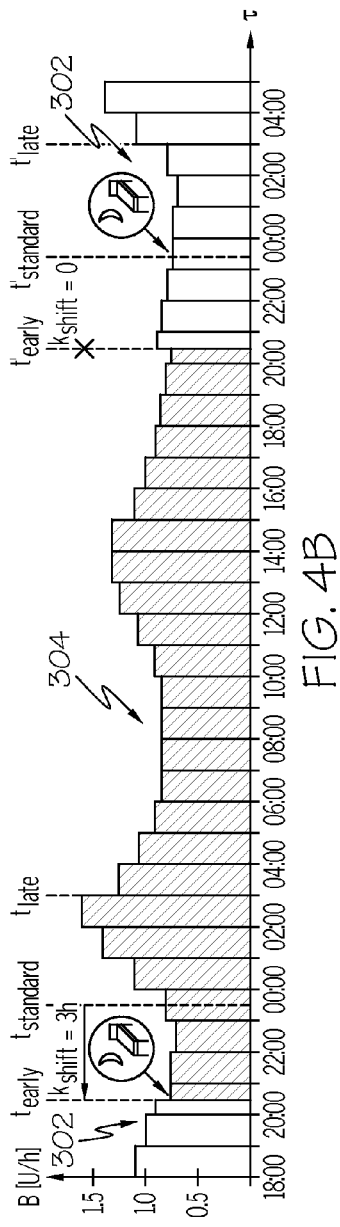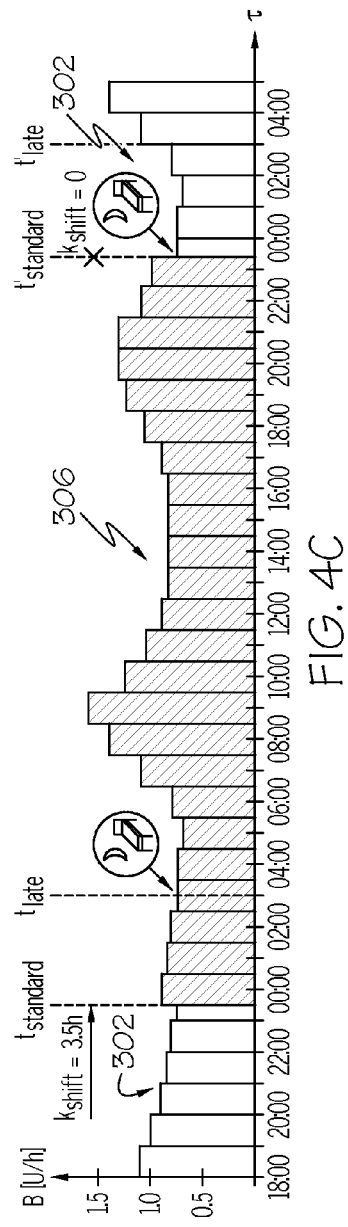

DIABETES THERAPY DEVICE ENABLING SHIFTING OF PARAMETER PROFILES

CROSS-REFERENCE TO RELATED APPLICATIONS

This application claims the benefit of European Patent Application 09012182.3 filed Sep. 25, 2009, which is herein incorporated fully by reference.

TECHNICAL FIELD

The present disclosure is related to devices for diabetes therapy, and in particular to insulin infusion devices, such as insulin pumps, and diabetes management devices.

BACKGROUND

Diabetes therapy devices form a basis for therapy of Diabetes Mellitus. In particular, miniaturized insulin pumps are used in the CSII (Continuous Subcutaneous Insulin Infusion) therapy. Such an insulin pump is disclosed, for example, in WO 2003053498 A2, to which reference is made for the general design and features of insulin pumps.

Besides insulin pumps, syringes or pen-like injection devices may also be used as diabetes therapy devices for the self-administration of insulin. Other diabetes therapy devices are diabetes management devices. These look similar to a cell phone or a Personal Digital Assistant and may be used for calculating insulin amounts and for diary-keeping purposes.

In comparison to alternative therapy forms with one or multiple daily insulin injections, CSII therapy is generally superior with respect to the resulting therapy quality. This is mainly caused by the fact that in CSII therapy, an insulin pump administers a so-called "basal" insulin rate autonomously in a quasi-continuous way night and day, thus meeting the diabetic's time-of-day dependent basal insulin demand. The basal insulin demand is the diabetic's insulin demand for maintaining the body metabolism according to a generally circadian chronobiological cycle, independent of food intake. The required basal infusion rate according to the circadian basal insulin demand as well as other parameters that may be stored in the parameter profile are inherent for a specific diabetic, and are generally independent of the occurrence of further therapy-related events, such as food-intake. Those other parameters may show some long-term variation and may require modification from time to time, typically every few years, or at a general change of the diabetics overall daily routines and lifestyle.

In addition to the basal insulin demand, bolus insulin is required by a diabetic to compensate for carbohydrate intake and other exceptional conditions. These additional insulin boli can be infused by an insulin pump on demand.

Therefore, devices that store an adjustable infusion rate profile as a function of the time of day may result in therapy quality that is not satisfying in some cases, resulting in long-term complications as well as potentially dangerous short-term excursions of the diabetic's blood glucose level. Particularly, such devices may not be suitable for diabetics who have a variable personal lifestyle and variations in their daily routine.

SUMMARY OF INVENTION

In accordance with one embodiment, a diabetes therapy device is disclosed. The diabetes therapy device includes a profile memory. The profile memory stores a parameter profile and a dedicated reference time mark. The parameter profile defines at least one parameter that is associated with insulin administration as a function of time for a generally circadian chronobiological cycle. The reference time mark indicates the beginning of the circadian chronobiological cycle and initializes a running time. The diabetes therapy device also includes a controller unit. The controller unit is coupled to the profile memory and determines insulin amounts to be administered as a function of the running time in accordance with a current matching of the parameter profile and the running time. The determined insulin amounts are based on the at least one parameter, and the controller unit modifies the current matching of the parameter profile and the running time. The controller unit receives trigger information that is indicative of an upcoming cycle trigger event occurring at an upcoming trigger time. The upcoming cycle trigger event is a defined event that generally occurs once per day and triggers the beginning of the generally circadian chronobiological cycle. The controller unit computes a modified matching based on the reference time mark and the upcoming trigger time. The modified matching is time-shifted from the current matching. The controller unit also applies the modified matching by making the modified matching the current matching, such that future insulin amounts to be administered are determined in accordance with the modified matching.

In accordance with another embodiment, a diabetes therapy device is disclosed. The diabetes therapy device includes a profile memory. The profile memory stores a parameter profile and a dedicated reference time mark. The parameter profile defines at least one parameter that is associated with insulin administration as a function of time for a generally circadian chronobiological cycle. The reference time mark indicates the beginning of the circadian chronobiological cycle and initializes a running time. The diabetes therapy device also includes a controller unit and a going-to-bed sensor. The controller unit is coupled to the profile memory and determines insulin amounts to be administered as a function of the running time in accordance with a current matching of the parameter profile and the running time. The determined insulin amounts are based on the at least one parameter. The controller unit modifies the current matching of the parameter profile and the running time. The controller unit receives trigger information that is indicative of an upcoming cycle trigger event occurring at an upcoming trigger time. The upcoming cycle trigger event is a defined event that generally occurs once per day and triggers the beginning of the generally circadian chronobiological cycle. The upcoming cycle trigger event is associated with the diabetic going to bed, falling asleep or waking up. The going-to-bed sensor is operatively coupled to the controller unit, detects at least one of the following actions: falling asleep, being asleep, waking up, getting up, or an auxiliary event, wherein the occurrence of the auxiliary event is correlated with falling asleep, being asleep, waking up, or getting up. The controller unit also computes a modified matching based on the reference time mark and the upcoming trigger time, wherein the modified matching is time-shifted from the current matching. The controller unit applies the modified matching by making the modified matching the current matching, such that future insulin amounts to be administered are determined in accordance with the modified matching.

In accordance with yet another embodiment, a method of treating diabetes is disclosed. The method includes providing a profile memory. The profile memory stores a parameter profile and a dedicated reference time mark. The parameter profile defines at least one parameter that is associated with insulin administration as a function of time for a generally circadian chronobiological cycle. The reference time mark indicates the beginning of the circadian chronobiological cycle and initializes a running time. The method also includes providing a controller unit. The controller unit is coupled to the profile memory and determines insulin amounts to be administered as a function of the running time in accordance with a current matching of the parameter profile and the running time. The determined insulin amounts are based on the at least one parameter. The controller unit modifies the current matching of the parameter profile and the running time. The method also includes receiving trigger information that is indicative of an upcoming cycle trigger event occurring at an upcoming trigger time. The upcoming cycle trigger event is a defined event that generally occurs once per day and triggers the beginning of the generally circadian chronobiological cycle. The method also includes computing a modified matching based on the reference time mark and the upcoming trigger time. The modified matching is time-shifted from the current matching. The method also includes applying the modified matching by making the modified matching the current matching, such that future insulin amounts to be administered are determined in accordance with the modified matching.

These and additional advantages and features provided by the various embodiments of the present invention will be more fully understood in view of the following detailed description, in conjunction with the drawings.

BRIEF DESCRIPTION OF THE DRAWINGS

The following detailed description of the embodiments of the present invention can be best understood when read in conjunction with the following drawings, where like structure is indicated with like reference numerals, and in which:

FIGS. 4A-4C illustrate various insulin infusion rates as a function of time in accordance with one or more embodiments;

Figure 1A:
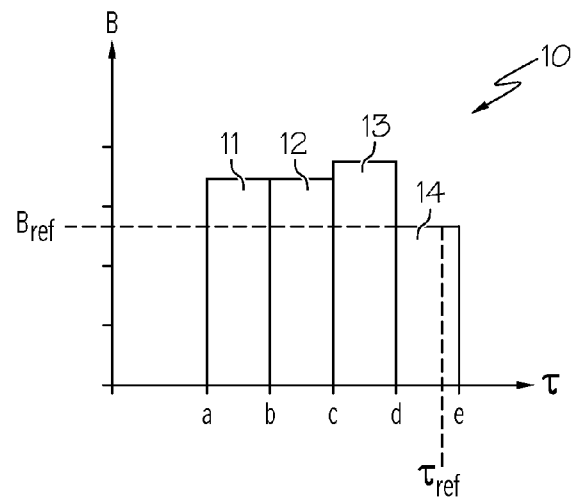
FIGS. 1A and 1B show exemplary infusion rate profiles and corresponding infusion rates as a function of time in accordance with one or more embodiments.

The embodiments set forth in the drawings are illustrative in nature and not intended to be limiting of the invention defined by the claims. Moreover, individual features of the drawings and invention will be more fully apparent and understood in view of the detailed description.

Skilled artisans appreciate that elements in the figures are illustrated for simplicity and clarity and have not necessarily been drawn to scale. For example, the dimensions of some of the elements in the figures may be exaggerated relative to other elements, as well as conventional parts removed, to help to improve understanding of the various embodiments of the present invention.

DETAILED DESCRIPTION

In the following, diabetes therapy devices are generally referred to as "devices" if no further specification is needed in the context. A particular focus is on insulin pumps and the present disclosure is mainly made with reference to insulin pumps for exemplary purposes without limiting or excluding other kinds of devices.

In accordance with one embodiment, a diabetes therapy device is disclosed. The diabetes therapy device includes a profile memory. The profile memory stores a parameter profile and a dedicated reference time mark. The parameter profile defines at least one parameter that is associated with insulin administration as a function of time for a generally circadian chronobiological cycle. The reference time mark indicates the beginning of the circadian chronobiological cycle and initializes a running time.

The diabetes therapy device also includes a controller unit. The controller unit is coupled to the profile memory and determines insulin amounts to be administered as a function of the running time in accordance with a current matching of the parameter profile and the running time. The determined insulin amounts are based on the at least one parameter, and the controller unit modifies the current matching of the parameter profile and the running time.

In one embodiment, the controller unit receives trigger information that is indicative of an upcoming cycle trigger event occurring at an upcoming trigger time. The upcoming cycle trigger event is a defined event that generally occurs once per day and triggers the beginning of the generally circadian chronobiological cycle. The controller unit computes a modified matching based on the reference time mark and the upcoming trigger time. The modified matching is time-shifted from the current matching. The controller unit also applies the modified matching by making the modified matching the current matching, such that future insulin amounts to be administered are determined in accordance with the modified matching.

The basal insulin demand of a diabetic is not considered as being strictly determined by the time of day. Instead, in one embodiment, the basal insulin demand is considered based on underlying generally circadian chronobiological cycles. The beginning of a new cycle is triggered by the occurrence of a cycle trigger event. A cycle trigger event is a defined event, in particular, an action or activity of the diabetic that generally only occurs once per day at typically similar times of day. In one embodiment, the time of occurrence of a cycle trigger event is referred to as trigger time. As will be described below in more detail, the diabetic falling asleep appears to be an especially suitable cycle trigger event. Other related events, however, such as the diabetic going to bed or awaking, may be used as cycle triggers as well in other embodiments.

The occurrence of the cycle trigger event has the physiological effect of triggering the beginning of a new chronobiological cycle. Once a cycle trigger event has occurred, the diabetic's basal insulin demand is determined as a function of running time by a given basal infusion rate profile until the occurrence of the following cycle trigger event. Some exceptions and deviations from this general rule are contemplated, and will be discussed below.

In the context of the present disclosure, the term "cycle" refers to a generally circadian chronobiological cycle as explained above. The term "generally circadian" indicates that the cycle length is typically approximately circadian, while some day-to-day variation typically occurs and larger deviations typically occur from time to time. That is, the actual cycle length is not exactly circadian but is typically approximately circadian for most of the days. Typical everyday-life examples of events with generally circadian occurrence are getting up, going to bed, having lunch, breakfast or dinner, and the like. While the actual cycle length accordingly shows some variation, the stored parameter profile has a fixed length that is favorably circadian. Thus, the stored parameter profiles, as well as the reference time mark, are not affected by a modification of the matching.

In another embodiment, a dedicated reference time mark is provided along with the infusion rate profile. The reference time mark is a defined point on the profile timescale identifying a specific point on the profile curve. The infusion rate corresponding to the reference time mark is considered as indicating the correct infusion rate according to which the insulin infusion should be performed on the occurrence of a cycle trigger event. The subsequent insulin infusion is, at least for some time, obtained by the infusion rate profile from the reference time mark point on.

Figure 1B:
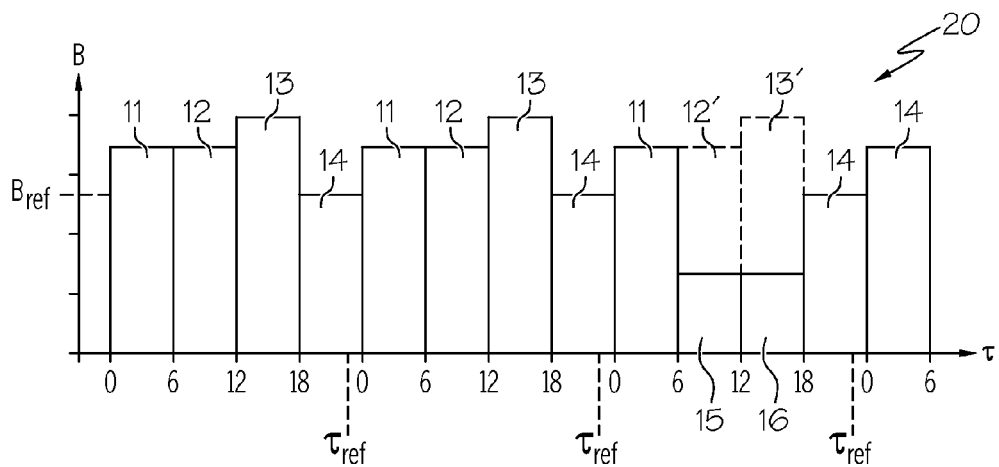

Referring to FIGS. 1A-1B for example, a reference time mark is shown and is indicated as $\tau_{ref}$. The corresponding infusion rate is symbolized as $B_{ref}$. The corresponding points of the running time in FIG. 1B are indicated as "$t_{ref,\,1}$, $t_{ref,\,2}$, $t_{ref,\,3}$ . . . and have the same cycle interval as the infusion rate profile.

For clarity reasons, "$\tau$" is generally used as symbol for times on the profile timescale, while "t" is used for points of time of the running time. "$\tau$" can accordingly be considered as indicating a time of day, while "t" indicates a time of day at a certain calendar date. If a time of day is referenced with "t", e.g. "t=20:00", it corresponds to that time of day at a specific date, whereas "$\tau$=20.00" indicates the time of day in general.

In one configuration and embodiment, the insulin infusion is controlled in function of time according to a variable matching of the infusion rate profile and the running time in dependence on the occurrence of cycle trigger events. The insulin infusions corresponding to the cycle trigger events are time-shifted with respect to each other and can be obtained by shifting the insulin rate profile in the time-domain. Cycle trigger events may occur in time intervals that change, with some longer and some shorter.

Medical considerations and experience suggest that the same relation as discussed above with respect to the basal infusion rate holds true for other parameters in an analogue way. Within the present context, the term "parameter" may refer to any time dependent parameter which follows a generally circadian chronobiological cycle as discussed above and which is used for determining insulin amounts to be administered to a diabetic person.

As will be shown below, the information that is indicative for a cycle trigger event may be received by the controller unit 110 directly at the trigger time or may be received in advance. The diabetes therapy device 100 generally comprises elements or assemblies for receiving the information that is required for computing a modified matching as will be discussed below.

In some embodiments, the diabetes therapy device 100 may comprise an insulin pump with a pump unit 104. In this case, the at least one parameter comprises a basal infusion rate and the parameter profile comprises a basal rate profile. In such an embodiment, the controller unit 110 is configured to control insulin infusion by the pump unit as a function of running time in accordance with the current matching.

In some embodiments, the controller unit 110 computes the modified matching such that the reference time mark $\tau_{ref}$ is aligned with the trigger time. In those embodiments, the reference time mark $\tau_{ref}$ is passed at the trigger time. In alternative embodiments, the modified matching is computed such that there is a time interval, for example a constant delay time, between the trigger time and passing of the reference time mark $\tau_{ref}$. Both kinds of embodiment will be discussed in more detail below.

Medical considerations suggest the diabetic person falling asleep to trigger the beginning of a new chronobiological cycle. Accordingly, the reference time mark $\tau_{ref}$ in FIGS. 1A-1B may be associated with the diabetic falling asleep and the corresponding infusion rate $B_{ref}$ is the required infusion rate when falling asleep.

A variety of methods and sensor setups are known in the art for detecting if a person has fallen or is falling asleep. The sensor may especially be reactive on one or multiple of the physical motion, the body temperature, the electrical skin impedance, or ECG or EEG values. All of those parameters are known to reflect falling asleep.

The application of those sensors, however, requires considerable effort with respect to sensor and electronics hardware, evaluation algorithm as well as handling. Those efforts may not be justified, especially if a diabetic generally follows a largely fixed schedule from which deviations only occur from time to time.

Therefore, an auxiliary event and an auxiliary time which are related to falling asleep may be provided and received by the controller unit 110, in particular the time of going to bed. A delay time may be stored by the controller unit 110 and may be considered to compensate for an estimated time difference between the time of going to bed and the time of falling asleep. The delay time is advantageously an adjustable parameter.

For example, a going-to-bed sensor may be provided, the going-to-bed sensor being operatively coupled to the controller unit and being designed to detect if the diabetic is going or has gone to bed. A cost and energy efficient setup may be based on the reduced physical motion in this case. A corresponding device is disclosed, for example, in the EP 2108393 A1. Instead of going to bed or falling asleep, getting up or awakening may be detected in a similar way.

In some embodiments, the ambient light intensity may be used to derive an auxiliary time. The diabetic may be assumed to have gone to bed, for example, if the light intensity falls below a given lower threshold intensity for a given threshold time. In some embodiments, different kinds of auxiliary data are considered in combination to determine an occurrence of the cycle trigger event.

As cost-efficient alternative, the device may comprise a "going-to-bed" button which the diabetic operates each time when going to bed. In this case, a delay time is favorably considered as described above.

Alternatively or additionally to providing a sensor and/or a button, the controller unit may be configured to receive cycle trigger information via a user interface or a data exchange interface of the device.

A typically present user interface 130 of the device 100 may be used for manually entering the expected future trigger time or an auxiliary time, such as the diabetic's expected time of going to bed. In a similar way, the expected point in time for the occurrence of a cycle trigger event may be entered into a further device, such as a remote controller or a diabetes management device and transmitted to the insulin infusion device via a data interface. While being somewhat less convenient than a sensor or a dedicated button, manually entering expected trigger times requires the minimum hardware effort, if any. Additionally or alternatively, the data interface may be used to couple the device to an external sensor, such as a going-to-bed sensor, which transmits the occurrence of a cycle trigger event to the diabetes therapy device.

In some embodiments, the profile memory 116 is configured to additionally store a standard matching of the parameter profile and to modify the matching by making this standard matching the current matching.

Such an embodiment is especially favorable for diabetics who normally follow a largely fixed daily standard routine and therapy schedule from which significant deviations only occur from time to time.

If the reference time mark $\tau_{ref}$ on the profile timescale is passed while the standard matching is active, a cycle trigger may be assumed to have occurred without requiring any corresponding input.

Along with the diabetic returning to the normal daily routine, for example on the following day, he or she can command the device 100 to resume the standard matching. Alternatively or additionally, the device 100 may be configured to automatically resume the standard matching.

In alternative embodiments, no standard matching is provided and the controller unit 110 receives cycle trigger information individually for each beginning of the chronobiological cycle, on a day-to-day basis. This type of embodiment is especially favorable for automated systems where an occurrence of the trigger event is detected by a sensor as described above.

In some embodiments, the controller unit 110 is configured to temporarily control the determination of insulin amounts to be administered in accordance with a transition profile 306', 308', wherein determination according to the transition profile bridges determination according to the current matching and according to the modified matching.

A transition profile 306', 308' may be advantageous especially for the following several reasons. Simply modifying the matching at a fixed point in time generally results in a "jump" in the therapy parameter. A transition profile 306', 308' may therefore be introduced for smooth the transition. Furthermore, individual cycles may be longer than the cycle length of the profile, in particular longer than 24 h. Accordingly, a "gap" may exist in which the parameter is not clearly defined by the profile. A transition profile may therefore be used to fill the gap.

Since a transition profile 306', 308' does generally not fully reflect the diabetic's actual physiological state, the time span covered by a transition profile 306', 308' may be limited to a maximum value that is smaller than the circadian cycle length, for example, 12 hours or 6 hours.

The transition profile 306', 308' may especially be either of a constant or a section of the parameter profile as stored by the profile memory 116. In some embodiments, the device is configured to temporarily block modifying the matching. Medical considerations suggest the existence of a minimum cycle interval which starts every time a new chrono-biological cycle is started. A next cycle can not start before this minimum cycle interval has lapsed, even if a cycle trigger event occurs. The controller unit 110 may therefore be configured to block modifying the matching if the time difference of the trigger point in time, that is, the occurrence of a cycle trigger event, to the last previous occurrence of a cycle trigger event is below a minimum cycle interval. The last previous cycle trigger event may have been associated with a modification as described above or may be a cycle trigger event that is assumed to have occurred due to the running time passing the reference time mark $\tau_{ref}$.

In some embodiments, the controller unit 110 is configured to block the applying of a modified matching if the time difference of the reference time mark $\tau_{ref}$ before and after applying the modified matching is smaller than a threshold time difference. This is equivalent to modifying the matching being blocked if it would result in a shifting which is smaller than the threshold time difference.

Introducing a threshold time difference below which the matching is not modified is considered as being favorable in order to avoid small modifications which add to the overall therapy variability without having a significant positive effect. The threshold time difference may have an absolute value of about 1 hour and is advantageously a configurable parameter.

In some embodiments, the controller unit 110 is configured to modify the matching without having received information indicative of a cycle trigger event under certain circumstances.

Medical considerations suggest that the beginning of a new cycle of the diabetic's body is triggered if the diabetic stays awake for an untypically long time. In this case, there is no trigger event such as falling asleep that would trigger the beginning of the cycle. Instead, it is triggered by a "body internal clock".

In some embodiments, the controller unit 110 is configured to repeatedly modify the matching. In embodiments where the basal insulin infusion is normally controlled in accordance with a standard matching, resuming the standard matching can be considered as a further modification. This further modification follows a first modification by which the standard matching was modified. In embodiments where no standard matching is provided, the modification is favorably done on a day-to-day basis as described above.

The controller unit 110 may especially be configured to receive information indicative of a further trigger event and to modify the matching if the difference of the current point in time to a previous occurrence time of the further trigger event exceeds a maximum awake interval without a cycle trigger event having occurred since the previous occurrence of the further event.

The further trigger event may be the event of awaking or an auxiliary trigger event which is indicative for the occurrence of the further trigger event, such as the cycle trigger event of getting up. In some embodiments, sensors are used to detect the occurrence of the further cycle trigger events or a corresponding auxiliary cycle trigger event. The sensor may especially be a sensor which is also used for detecting an occurrence of the cycle trigger event. For example, the physical activity of the diabetic may be used for both detecting the trigger event of going to bed and/or falling asleep and to detect the trigger event of getting up and/or awaking. In some embodiments, the ambient light intensity is used to derive an auxiliary time. The diabetic may be assumed to have got up, for example, if the light intensity exceeds a given upper threshold intensity for a given threshold time. A maximum awake interval of about 26 hours is contemplated, but other time periods are contemplated such as 20 hours, 24 hours, 28 hours, or 36 hours. Advantageously, the maximum awake interval is a configurable parameter.

As stated above, further parameters besides a diabetic's basal insulin demand vary in accordance with the same chrono-biological cycle. The set of parameters may therefore comprise those further parameters and the reference time mark may be common for all parameters, such that the same modification rules are applied for those parameters.

In some embodiments, the set of parameters comprises at least one of a carbohydrate factor and a blood glucose correction factor. Carbohydrate factors and blood glucose correction factors are examples for parameters that may be considered additionally or alternatively to the basal rate.

A carbohydrate factor reflects the typically proportional relationship between the carbohydrate intake by the diabetic and the bolus insulin amount which has to be administered for processing the carbohydrates. Similarly, a blood glucose correction factor reflects the relationship between an undesirably raised blood glucose value and the bolus insulin amount, which has to be administered for the blood glucose value to return into a desired target range or to a desired target value.

Carbohydrate factors and blood glucose correction factors are typically used by bolus calculation algorithms which compute an insulin bolus to be administered based on a carbohydrate amount the person with diabetes intends to eat and/or based on a measured blood glucose value. Exemplary approaches and algorithms may be found in the disclosure of WO 2006/066926, which is herein incorporated by reference in its entirety. Those algorithms may be modified in accordance with the present disclosure.

An appropriate bolus amount in order to compensate for a given intake of food may, following a basic algorithm, be computed by multiplying the carbohydrate factor with the carbohydrate amount of the food. While the carbohydrate factor is defined by parameter profile, the actual bolus amount accordingly depends on both the parameter profile and the carbohydrate amount of a specific meal that the diabetic intends to eat. The same holds true, mutatis mutandis, for a bolus that is computed and infused for blood glucose correction purposes. In accordance with some more advanced approaches, further influence factors, such as the time and amount of past insulin infusions, the composition of meals, and the like.

A diabetes therapy device 100 storing carbohydrate factors and/or blood glucose correction factors may, for example, be an insulin pump with integrated bolus calculation capabilities. Alternatively, it may be a separate device, such as a diabetes management device, or a PDA or cell phone running a corresponding program, which is integrated with the diabetes therapy device of the present disclosure.

If the diabetes therapy device 100 is not an insulin pump and is not coupled to an insulin pump, the actual insulin administration is typically carried out manually with an insulin pen, a syringe, or the like, when required due to a meal and/or for correction purposes. Here, the determined bolus amount is typically displayed by a display of the device or otherwise indicated.

In some embodiments, the parameter profile only defines a single parameter. If the diabetes therapy device 100, is, for example, an insulin pump, the only parameter may be a basal infusion rate. If the device is a blood glucose meter, the only parameter may be a blood glucose correction factor. In the context of a more complex system, however, a number of parameters is generally used.

The functional components of the device 100 are not necessarily all integrated into the same single physical unit. If the device 100 is, for example, an insulin pump, it may be split into a remote controller and an infusion unit. A remote controller may be present for convenient and discrete operation. For such embodiments, the controller unit 110 is advantageously also split. The remote controller may also integrate further components and/or modules such as a blood glucose meter or a diary-keeping module. The remote controller may further include a bolus calculation module for calculating of insulin boli based on meal factors and blood glucose level correction factors as described above. For such embodiments, the modification of the corresponding therapy parameters is advantageously also carried out by the remote controller.

As background for understanding the present disclosure, reference is now made to FIGS. 1A-1B. FIG. 1A shows an exemplary basal infusion rate profile 10 with basal infusion rates B as function of time on a profile timescale with $\tau$ as time parameter, wherein each point of the profile is defined by a pair (B, $\tau$) of an infusion rate B and a corresponding time $\tau$ on the profile timescale. The cycle is circadian, that is, the total cycle length is 24 hours. For a circadian cycle, the time parameter $\tau$ is directly associated with the time of day. The exemplary profile comprises four segments 11, 12, 13, 14. Each two adjacent segments define basal infusion rates for corresponding adjacent time intervals. The starting and ending times of the single intervals are indicated by "a", "b", "c", "d", or "e". In the example, each interval has 6 hours duration. However, other interval durations are also contemplated. The profile is typically stored by a profile memory 116 in form of a list or table.

It should be noted that the four different rates as shown in FIG. 1A are exemplary. In practice, the list may typically have 24 elements or 48 elements, with each element defining a basal infusion rate for 1 hours or 30 minutes of a circadian cycle.

Instead of time intervals of equal length, the time intervals may alternatively have different lengths. Furthermore, the infusion rate profile may be stored in a different form, for example as parameter set of a continuous interpolation function according to which the infusion is controlled in a smooth way without "jumps" of the rate B.

FIG. 1B shows an exemplary infusion rate 20 as a function of the running time which results from continuously cycling through the infusion rate profile 10 of FIG. 1A. For clarity reasons, the running time is referred to with the symbol "t" as time parameter.

In one embodiment, the profile is matched to the running time such that each of the relative times "a" . . . "e" corresponds to a certain time of day. In FIG. 1B, the matching is such that "a" corresponds to midnight, "c" corresponds to noon and "e" corresponds to midnight of the next day. By time-shifting the profile on the time axis, any other matching may be obtained as well.

On the third of the three days shown in FIG. 1B, the infusion is modified to a constant infusion rate from hour 6 to hour 18, as indicated by the segments 15, 16. The dashed elements 12' 13' indicate the replaced infusion rates according to the profile 10 without modification. Those modifications may be controlled by the user on demand, for example to deal with special situations, such as extended sportive activities. An infusion with such temporary modifications is still considered as "generally cyclic".

Figure 2:
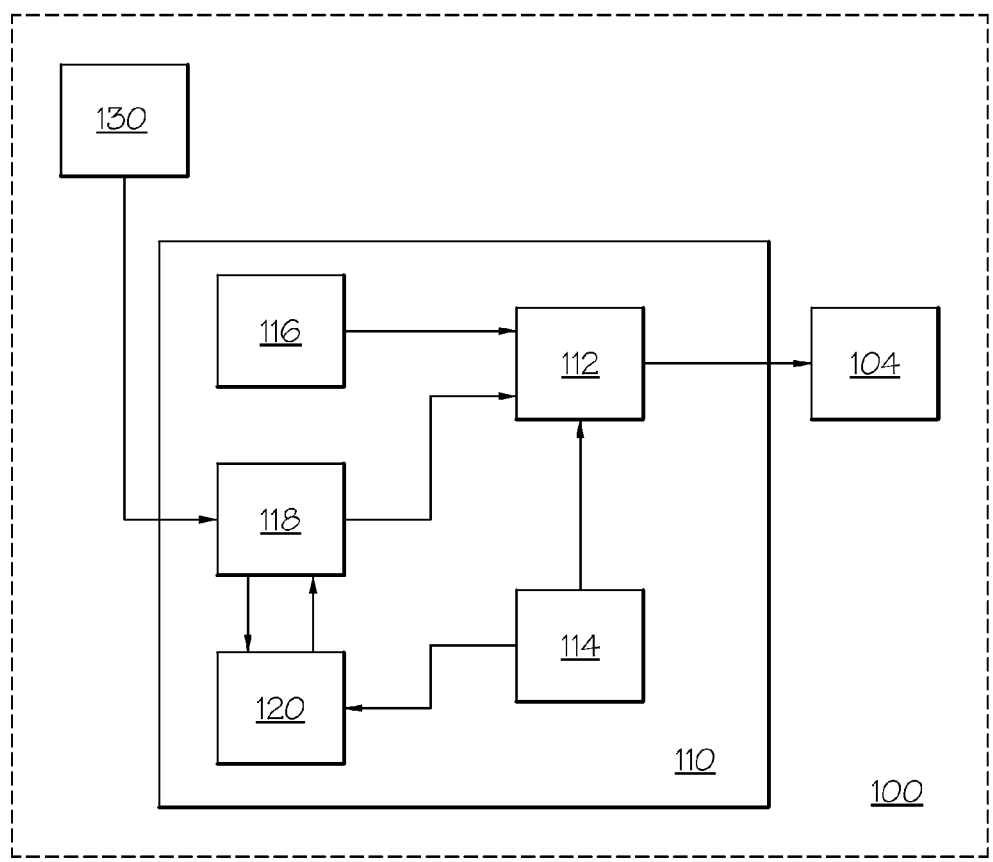
FIG. 2 shows a schematic view of an exemplary insulin pump in accordance with one or more embodiments.

FIG. 2 shows a schematic and structural view of an exemplary device 100 in accordance with yet another embodiment. It may comprise an electronic controller unit 110 which controls the overall operation of the device. The controller unit 110 is realized by state-of-the-art circuitry which is known for such applications and typically comprises one or multiple micro controllers and supplementary components. The controller unit 110 controls the operation of the pump unit 104. The pump unit 104 may be of the syringe-driver type as commonly used for insulin pumps or be of another design suited for insulin infusion, such as a micro membrane pump or a peristaltic pump.

In another embodiment, the device comprises a profile memory 116. The profile memory 116 may be non-volatile semiconductor memory. The profile memory 116 may store an infusion rate profile as described above and store a reference time mark. The reference time mark may be either stored explicitly in addition to the infusion rate profile or may be stored implicitly. In this latter case, the infusion rate profile is stored such that the reference time mark corresponds to a defined point on the profile timescale, for example noon, midnight or 23:00 as the typical time of going to bed. If the infusion rate profile is stored as a table of infusion rates as described above, the reference time mark may, for example, correspond to the beginning of the first interval.

The profile memory 116 may store a set of alternative infusion rate profiles from which an active infusion rate function can be selected in order to cope with different types of situations where the diabetic's basal insulin demand is different, for example, during holidays or vacations.

In yet another embodiment, the therapy device 100 may comprise an infusion control unit 112 to control the pump unit 104 for insulin infusion as a function of time in accordance with the infusion rate profile and a given matching of the profile timescale and the running time. The running time is provided by a clock unit 114.

The therapy device 100 may comprise a modification unit 118. The modification unit 118 is provided for computing a modified matching and a modified insulin infusion regime as function of time based on the infusion rate profile that is stored in the profile memory 116. The modified matching is transferred to the infusion control unit 112. An optional blocking unit 120 is provided for selectively blocking a modification.

In another embodiment, the therapy device 100 further comprises a user interface 130 for controlling and monitoring the system. The user interface 130 comprises an input unit in the form of buttons or the like, and an output unit with a display and an acoustical and/or tactile indicator. The user interface 130 may especially be used to enter data for a matching modification as will be described below.

The device 100 typically comprises further components, which are not shown in FIG. 2 since they are of no special relevance in the context of the present disclosure, such as a power supply, sensors for monitoring the operation of the device and one or multiple data exchange interfaces.

For clarity and simplicity reasons, the infusion rate is considered as sole parameter and the insulin pumps are considered as sole diabetes therapy devices in the following exemplary description. It will be appreciated, however, that additional or alternative parameters may be considered in an analogue way. If the device is not an insulin pump, some modifications off the exemplary devices are required which, however, are obvious for a person skilled in the art. In particular, the pump unit 104 may not be present in this case.

Figure 3:
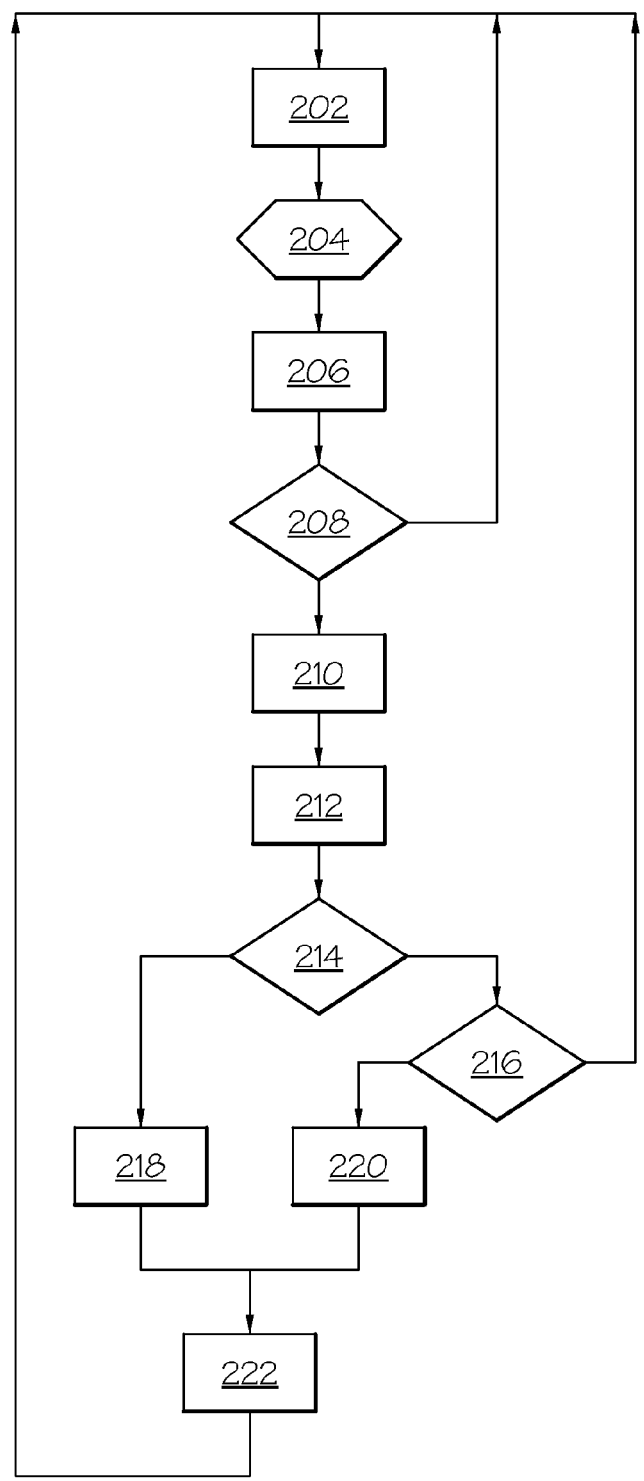
FIG. 3 shows an operational flowchart for the modification of an insulin infusion device in accordance with one or more embodiments.

In accordance with one embodiment, FIG. 3 shows the processing processing steps that are performed by an exemplary device 100 according to FIG. 2 for modifying the insulin infusion. In the following, it is first assumed that the therapy device 100 is designed to generally control the insulin infusion according to a standard matching.

In processing step 202, the device 100 either performs insulin infusion in accordance with the standard matching or according to an already modified matching that is different from the standard matching. During the following steps, insulin administration is continued in the same way as in processing step 202.

In processing step 204, the modification unit 118 receives a coming future bedtime $t_{bed}$ for going to bed next time. The coming bedtime is entered into the therapy device 100 via the user interface 130. For this purpose, a corresponding menu is advantageously provided, which may be selected by the diabetic when required for initiating processing step 204. It is assumed that the time at which processing step 204 is carried out, i.e., the coming bedtime, is provided sufficiently before the actual bedtime. The time at which the modified bedtime should be entered will be discussed in more detail later on.

In processing step 206, the last previous bedtime $t_{previous}$ is determined. If the current matching is different from the standard matching, the previous bedtime is typically a manually entered bedtime. Otherwise, it is the bedtime corresponding according to the standard matching.

In processing step 208, the operational flow branches in dependence of the absolute time difference $|t_{bed}-t_{previous}|$ between the previous bedtime and the coming bedtime as provided in processing step 204. If this time difference is below a minimum cycle time, the process of modifying the matching is blocked and the therapy device 100 returns to processing step 202. If a dedicated blocking unit 120 is present, it comprises a corresponding minimum cycle timer, which is triggered at each bedtime or each time the reference time mark is passed. In this case, the status of the minimum cycle timer is considered to determine if a modification should be allowed or should be blocked.

In processing step 210, the modification unit 118 computes a time shift $k_{shift}$. The time shift is the time difference between the coming actual bedtime as provided in processing step 204 and the next bedtime $t_{standard}$ that would result from further applying the standard matching, i.e., $k_{shift}=t_{bed}-t_{standard}$.

The time shift may be computed in any units, such as hours or minutes in dependence of the device architecture, taking into account that the calendar date of $t_{bed}$ and $t_{standard}$ may or may not be identical. The time shift $k_{shift}$ is positive if the bedtime is exceptionally late and is negative if the bedtime is exceptionally early as compared to the standard matching.

In processing step 212, an effective time shift $dk_{shift}$ is computed as the time shift between the coming bedtime and the next bedtime that would result from further applying the current matching. If the current matching is the standard matching, the effective time shift is equivalent to the time shift, i.e., $dk_{shift}=k_{shift}$. However, if the insulin infusion is currently being performed in accordance with a matching that is already different from the standard matching, the effective time shift is computed as correctly signed difference $dk_{shift}=k_{shift}-k_{shift,0}$ of the time shift as computed in step 210 for the coming going to bed and the currently active time shift $k_{shift,0}$.

In processing step 214, the effective time shift is compared to a positive threshold time difference $k_{min}^+$. If the effective time shift $dk_{shift}$ is larger than the threshold time difference, operation proceeds with processing step 218. If the effective time shift $dk_{shift}$ is not larger than the threshold time difference, it is compared with a negative threshold time difference $k_{min}^-$ in processing step 216. If the effective time shift $dk_{shift}$ is smaller than the negative threshold time difference, operation proceeds with processing step 220, otherwise, no modification of the insulin infusion as a function of time is performed and the infusion is continued according to the current matching in processing step 202. In combination processing step 214 and processing step 216 have the effect that a modification will be performed only if the modification results in a shift, as compared to if the current matching exceeds a value given by the positive and the negative threshold time difference value. The threshold time differences may, for example, be chosen symmetrically to $k_{min}^+=1$ h and $k_{min}^-=-1$ h.

The processing steps 218, and 220 are delay steps which are carried out until the running time "t" equals the point in time $t_{modify}$ at which the modified matching is to be applied, thus making it the current matching.

In case of the effective time shift being negative, i.e., the diabetic goes to bed earlier as compared to the previous day, the modified matching is applied at the coming bedtime as provided in processing step 204, i.e., $t_{modify}=t_{bed}$. That is, in processing step 220 the condition $t=t_{bed}$ is detected.

In case of the effective time shift being positive, i.e., the diabetic going to bed later as compared to the previous day, the modified matching is applied at a point in time which is $dk_{shift}$ before the coming bedtime, i.e., $t_{modify}=t_{bed}-dk_{shift}$. That is, in processing step 218 the condition $t=t_{bed}-dk_{shift}$ is detected. This point in time equals the time at which the reference time mark would be passed without the modification. The rationale for selecting the point in time for applying the modified matching will be discussed below.

In processing step 222, the modified matching is actually applied by making it the current matching and the insulin infusion is continued in accordance with the modified matching in processing step 202.

FIGS. 4A-4C exemplarily illustrate the insulin infusion as a function of time according to two alternative scenarios. For reference purposes, the bars 302 in FIG. 4A represent the infusion over the running time "t" according to a standard matching, with the bars 302 indicating the hourly basal infusion rate B for each hour of the day in Units per Hour [U/h]. The diabetic typically goes to bed at a standard bedtime $\tau_{standard}=23:30$ with $t_{standard}$, $t'_{standard}$ indicating the corresponding standard bedtimes of two consecutive days. The reference time mark is associated with the standard bedtime $\tau_{standard}$, too. The standard matching is accordingly such that the reference time mark is passed at 23:30 every day.

The FIG. 4B shows the infusion as a function of time when the diabetic decided to go to bed 3 h early as compared to the bedtime, i.e., at $t_{bed}=t_{early}=20:30$. The coming bedtime has to be provided as described above in the context of FIG. 3 shortly before the early bedtime or at any still earlier point in time. The modified matching is such that the reference time mark is aligned with the early bedtime. That is, the infusion rate profile is time-shifted about $k_{shift}=-3$ hours as compared to the standard matching. As described in the context of FIG. 3, the point in time $t_{modify}$ for modifying the matching equals the early bedtime, i.e., $t_{modify}=t_{early}$. After applying the modified matching, insulin infusion is performed according to the time-shifted infusion rate profile, as indicated by the hatched bars 304 in FIG. 4B.

The next day, the diabetic returns to the usual schedule such that $t_{bed}=t'_{standard}$. The standard matching shall accordingly be resumed. The standard matching is applied at $t'_{early}$, that is, at a point in time which precedes the standard bedtime $t'_{standard}$ by the time shift of the previous day.

It can be seen that the insulin infusion is controlled in accordance with the non-standard matching for 24 hours i.e., one cycle interval of the infusion rate profile. Resuming the standard matching later, for example at the standard bedtime where the diabetic actually goes to bed the second day, may be performed as well. It would, however, result in the insulin infusion being controlled in accordance with a section of the infusion rate profile which reflects the basal insulin demand after falling asleep when the diabetic actually is still awake. The proposed point in time for resuming the standard matching, however, is not essential. Other points in time, in particular, earlier points in time could be chosen as well, for example noon.

FIG. 4C illustrates a situation where the diabetic decides to go to bed exceptionally late, at $t_{late}=3:00$. This situation is typical for a party event or the like. The corresponding time shift as compared to the standard bedtime is $k_{shift}=+3.5$ hours.

The modified matching is applied at $t_{modify}=t_{standard}$, i.e., at the time the diabetic would go to bed according to his normal schedule and the standard matching. After applying the modified matching, the insulin infusion is performed according to the time-shifted infusion rate profile, as indicated by the hatched bars 306. It should be noted that the standard bedtime $t_{standard}$ and $t_{bed}=t_{late}$ as the actual bedtime have different calendar dates.

In a similar way to the resumption to the standard matching as discussed above with reference to FIG. 4B, applying a modified matching before the actual bedtime $t_{late}$ prevents the insulin infusion being controlled in accordance with a section of the infusion rate profile, which reflects the basal insulin demand after falling asleep when the diabetic actually is still awake.

Like in the previous example, the diabetic returns to his regular routine, and, thus, the standard matching the following day. The standard matching is resumed immediately at the bedtime $t_{bed}=t'_{standard}$, resulting in the insulin infusion being correctly controlled when the diabetic actually goes to bed.

Figure 5A:
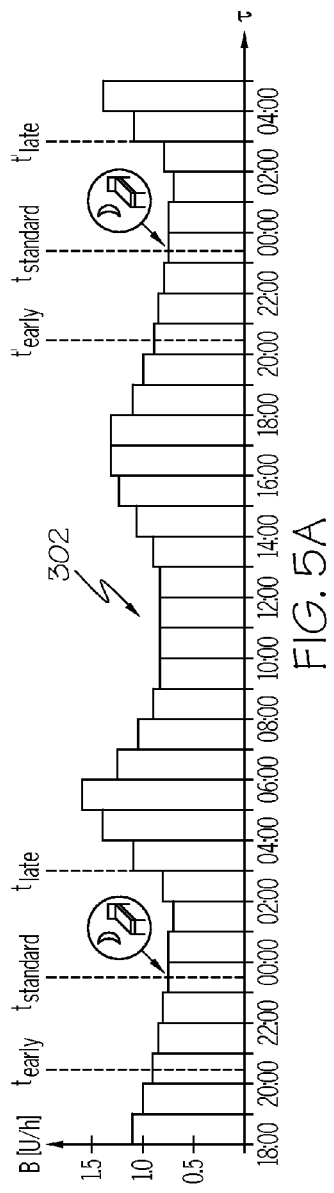
FIGS. 5A-5C illustrate various insulin infusion rates as a function of time in accordance with one or more embodiments.
Figure 5B:
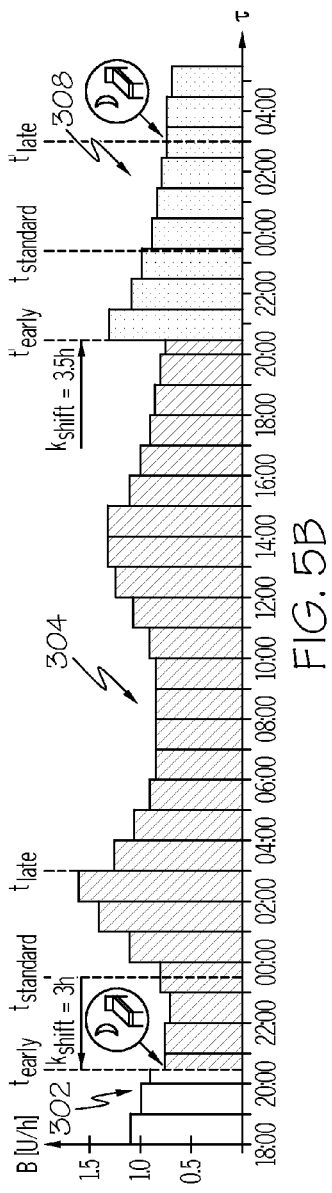
Figure 5C:
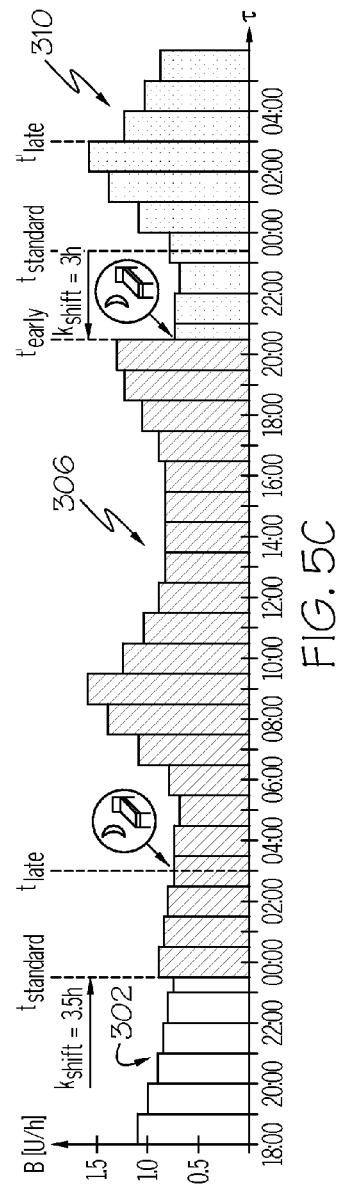

Two somewhat more complex situations are illustrated in FIGS. 5A-5C. For reference purposes, FIG. 5A represents the infusion over time according to a standard matching in the same way as FIG. 4A.

FIG. 5B illustrates a situation where the diabetic goes to bed exceptionally early, at $t_{bed}=t_{early}=20:30$, on a first day and goes to bed exceptionally late, at $t'_{bed}=t'_{late}=03:00$, the following second day. For going to bed early, modifying the insulin infusion as a function of time is carried out in the same way as described above with reference to FIG. 4B, as indicated by the bars 304.

For going to bed early on the first day, the corresponding time shift is $k_{shift}=-3$ hours. For going to bed late on the following day, the corresponding time shift is $k'_{shift}=+3.5$ hours. The resulting effective time shift for the second day is therefore $dk'_{shift}=k'_{shift}-k_{shift}=6.5$ hours, with the bars 308 indicating the shifted profile. In accordance with the computational rules given above with reference to FIG. 3, the second modification is applied at a point in time, which precedes the actual bedtime $t'_{late}$ by $dk'_{shift}$.

FIG. 5C illustrates an inverse situation where the diabetic goes to bed at $t_{bed}=t_{late}=03:00$ on the first day and on $t'_{bed}=t'_{early}=20:30$ the second day. For going to bed early, modifying the insulin infusion as a function of time is carried out in the same way as described above with reference to FIG. 4C, as indicated by bars 306. The second modification is performed when the diabetic actually goes to bed on the second day, at $t'_{early}$, the bars 310 indicating the correspondingly shifted profile.

Figure 6A:
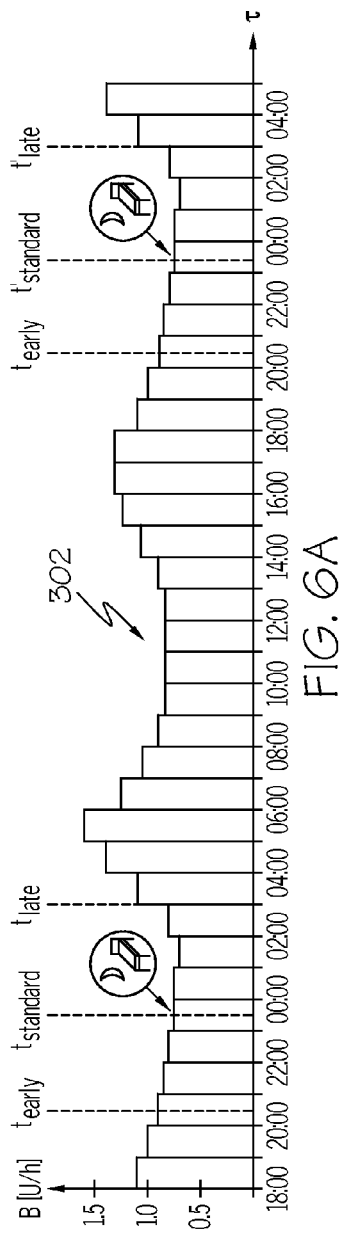
FIGS. 6A-6C illustrate various insulin infusion rates as a function of time in accordance with one or more embodiments.
Figure 6B:
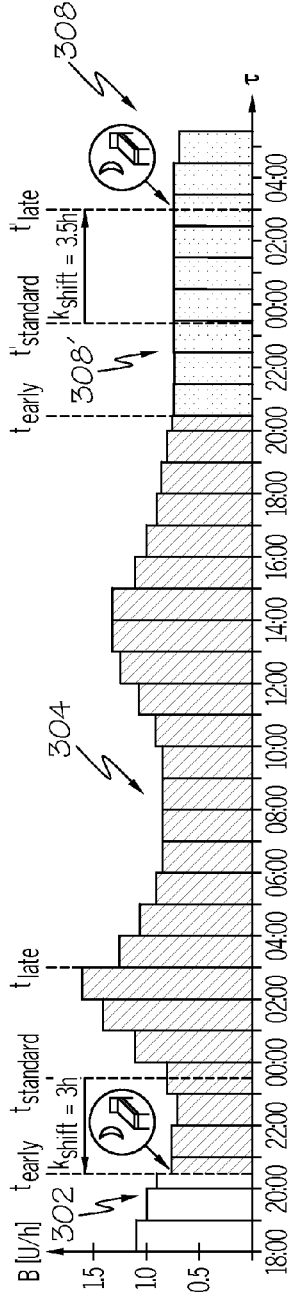
Figure 6C:
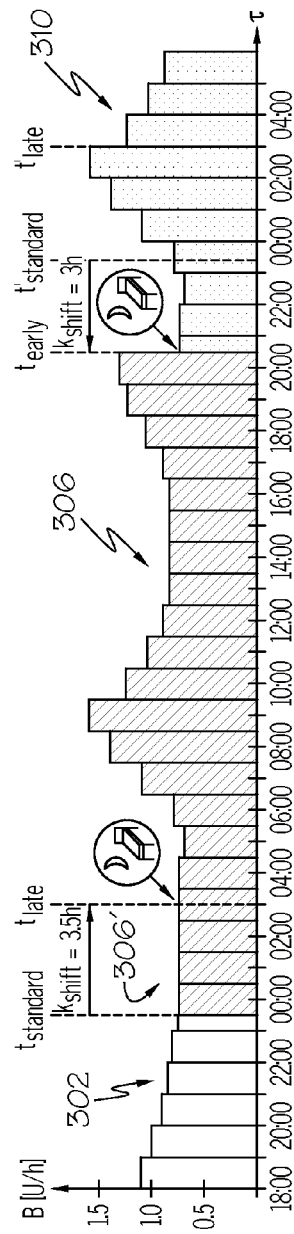

FIGS. 6A-6C illustrate the operation of an exemplary device in accordance with FIG. 2 where the transition between a current matching and a modified matching is carried out in a somewhat modified way as compared to FIGS. 3-5 and as discussed above. The following description is focused on those aspects which are different from the previously discussed examples.

Generally, FIGS. 6A-6C correspond to FIGS. 5A-5C. When the diabetic goes to bed later as compared to the previous day, the time interval between the beginning of two consecutive physiological cycles is longer than the circadian standard cycle interval of the infusion rate profile. In the examples shown in FIGS. 5A-5C, the resulting "gap" (from $t'_{early}$ to $t'_{late}$ in middle graph and from $t_{standard}$ to $t_{late}$ in the bottom graph) is filled by applying the modified matching some time before the actual bedtime $t_{bed}$, as indicated by bars 308'.

In the examples shown in FIGS. 6A-6C, a different approach is followed. Here, the modified matching is generally applied at the actual bedtime when a new cycle as defined by the reference time mark shall be started. The time "gap" between the ending of the previous physiological cycle and the beginning of the new cycle (from $t'_{early}$ to $t'_{late}$ in middle graph and from $t_{standard}$ to $t_{late}$ in the bottom graph) is filled by a constant infusion rate as transition profile, as indicated by the bars, 306', 308'.

If the infusion rate as defined by the infusion rate profile is identical on the left side of the reference time mark and the right side of the reference time mark, this infusion rate may advantageously be used as infusion rate for the transition interval. For an infusion rate profile which is made by segments of constant infusion rate, this is the case if the reference time mark is not aligned with the joint of two segments which define different infusion rates. This is the case, for example, in the examples of FIGS. 4-6 (see also $\tau_{ref}$ in FIGS. 1A-1B).

If the infusion rate as defined by the infusion rate profile is different on the left side and the right side of the reference time mark, either of those may be used for the transition period. Alternatively, other infusion rates, such as the average of both infusion rates, may be used as well.

In some cases, applying a modified matching results in a considerable "jump" or discontinuity of the infusion rate (see, for example $t'_{early}$ in FIGS. 5A-5C). This is typically not considered as being critical because the diabetic deviates from the usual schedule anyway and the insulin pharmacokinetics, as well as physiological reasons, cause a damping and smoothening of discontinuities. In dependence of the diabetic and the specific situation, the situation may be different. Therefore, a transition profile may be used in order to smooth the transition. The insulin infusion rate as a function of time may be considered as signal similar to voltages or the like with the applying of a modified matching resulting in a signal discontinuity. The modification unit may accordingly comprise a low pass unit of any desired characteristic to smoothen the transition. A transition period of about 1 hours to 3 hours may be preferable, but other transition periods are also contemplated.

Figure 7:
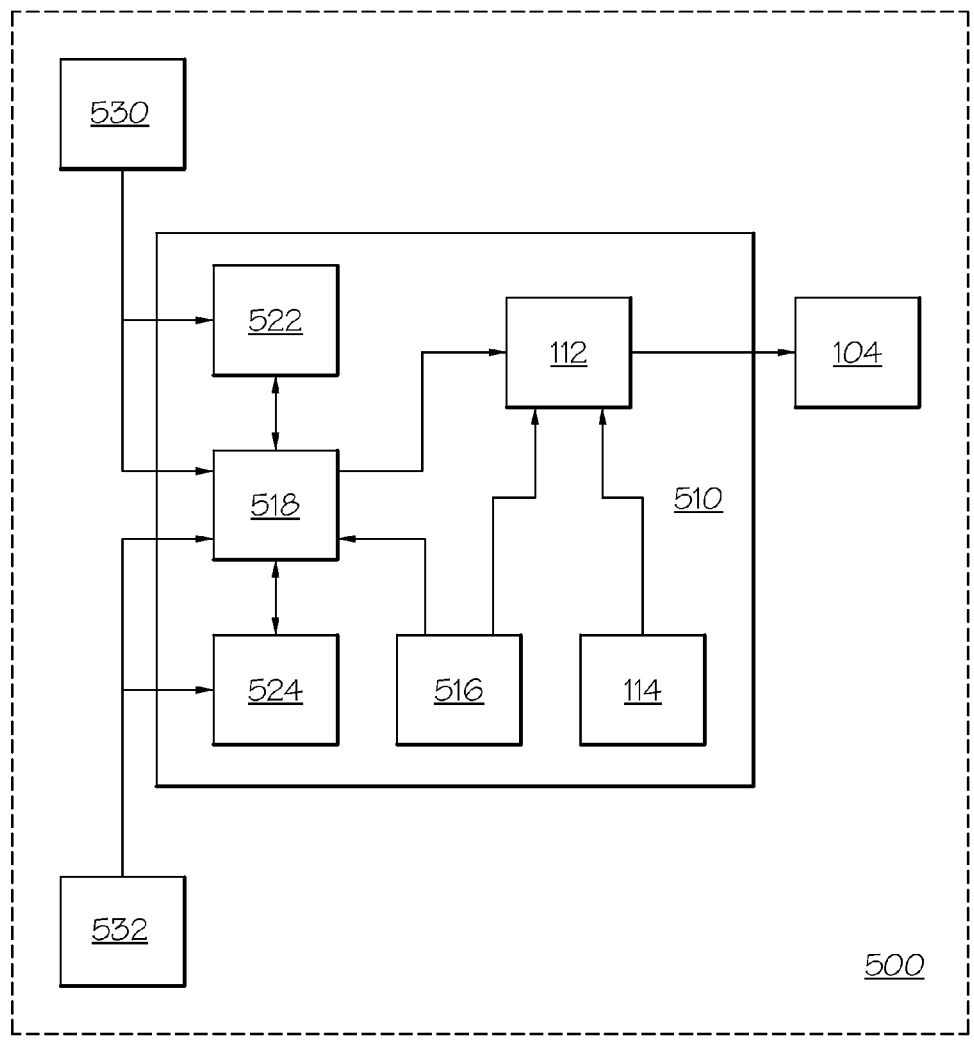
FIG. 7 shows a schematic of an insulin pump in accordance with one or more embodiments.

FIG. 7 shows a schematic and structural view of a further exemplary device 500 in accordance with the present invention. While some elements may be realized in substantially the same way as in the example of FIG. 2 discussed above, the operation of the modification controller and some related elements is different. The following discussion is focused on those aspects.

In contrast to the previously described embodiment, the device 500 is not configured for insulin infusion according to a standard matching. Instead, the modification unit 518, which forms a part of the controller unit 510 is configured to compute a new matching of the infusion rate profile with the running time for each beginning of a physiological cycle. Therefore, a going-to-bed sensor 530 is provided and operatively coupled to the modification unit 518. The going-to-bed sensor can be realized as described above in the general description of the invention. In an analogue way, a getting-up sensor 532 is provided and operatively coupled to the modification unit 518. The operation of this additional sensor will become visible in the discussion below. The sensors 530, 532 are shown as part of the device in FIG. 8, but may also be separate from the device and coupled to it via data interfaces.

Figure 8:
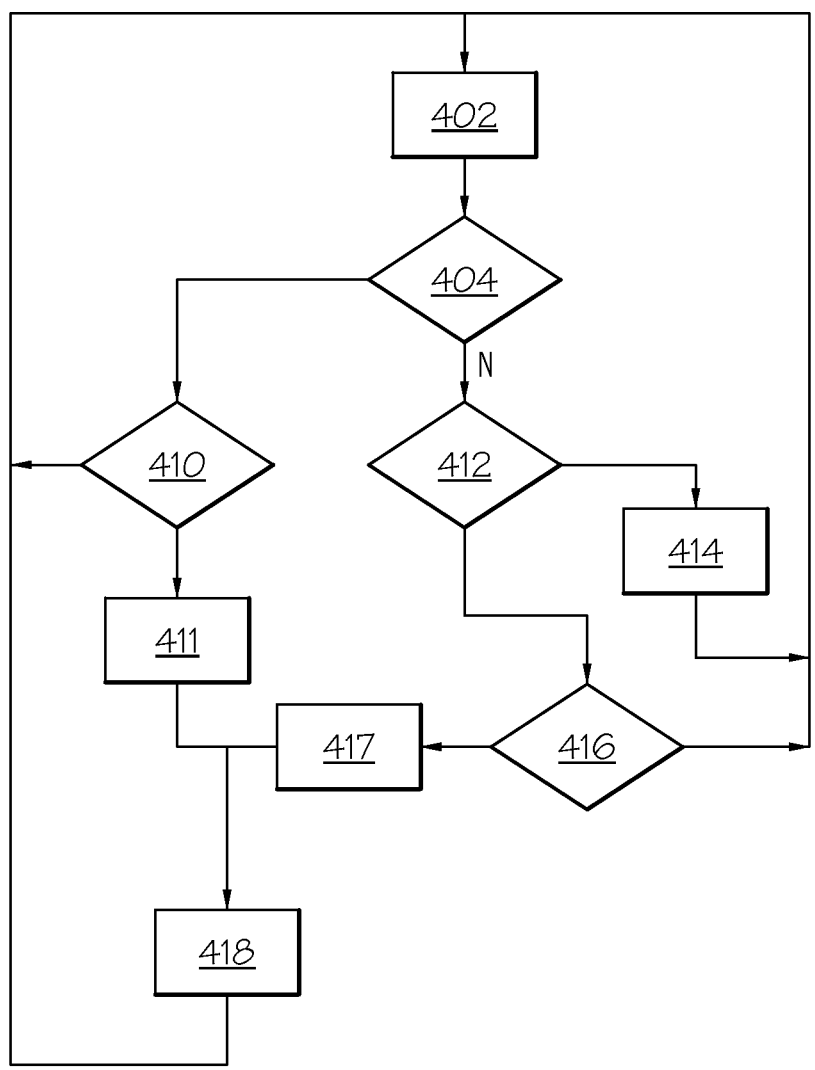
FIG. 8 shows an operational flowchart for modifying the insulin infusion in accordance with another embodiment.

While the going-to-bed sensor 530 and the getting-up sensor 532 are shown as separate elements in FIG. 8, they may also be realized as a single sensor, for example a physical motion sensor, which is evaluated for both the events of the diabetic going to bed and getting up.

Instead of sensors 530, 532, input devices such as buttons may be present which are pressed by the diabetic each time he goes to bed or gets up.

Instead of going to bed and getting up, the occurrence of auxiliary events may be detected by the sensors 530, 532 as discussed above in the general description of the invention.

A minimum-cycle-interval timer 522 and a maximum-awake-interval timer 524 are additional provided. The minimum-cycle-interval timer 522 blocks a modification of the insulin infusion as a function of time if the interval between a cycle trigger and the preceding cycle trigger is shorter than the minimum cycle interval. The maximum-awake-interval timer 524 indicates that a modification of the insulin infusion as a function of time should be initiated by the modification unit 518 autonomously if the maximum awake interval since the diabetic last getting up has passed without a cycle trigger having been detected in between. The maximum-awake-interval timer is active as long as the diabetic is awake.

Reference is in the following additionally made to FIG. 8, which illustrates the operation of the modification unit 518 and the related components of the device according FIG. 7.

In processing step 402, the infusion control unit 112 controls the insulin infusion in accordance with any current matching of the infusion rate profile and the running time. The following processing steps, which are related to the operation of the modification controller 518 are carried out in a repeated and substantially continuous way during the general operation of the device in processing step 402.

In processing step 404, the status of the going-to-bed sensor 530 is considered in order to determine if the diabetic is going to bed. If this is the case, the status of the minimum-cycle-interval timer 522 is considered in processing step 410. If the status of the minimum-cycle-interval timer 522 indicates that the time since the last cycle start is shorter than minimum cycle interval, no modification is performed and the regular operation is continued in processing step 402.

If the minimum cycle interval has lapsed, the maximum-awake-interval timer 532 is stopped in processing step 411 and a modified matching is computed and applied in processing step 418. Assuming that the reference time mark is associated with the bedtime, the modified matching is computed such that the reference time mark is aligned with the current time. Along with applying the modified matching, the minimum-cycle-interval timer is reset and the device returns to the normal operation in processing step 402.

If processing step 404 does not detect the event of the diabetic going to bed, the status of the waking-up sensor is considered in processing step 412. If an event of waking up is detected, the maximum-awake-interval timer 524 is reset and started in processing step 414 and the device returns to normal operation in processing step 402. It should be noted that no modification of the infusion occurs in this case.

If neither of the events of the diabetic going to bed or getting up is detected, the status of the maximum-awake-interval timer 524 is considered in processing step 416. If the maximum cycle time has elapsed, the maximum-awake-interval timer 524 is reset in processing step 417 and a modified matching is computed and applied in processing step 418 as described above.

It should be understood that the operational flow as shown in FIG. 8 as well as the hardware structure as shown in FIG. 7 are exemplary. For example, instead of relying on dedicated timers 530, 532, the points in time where the timers are reset according to the description as given above may be stored and compared with the current time as provided by the clock unit 114 later on. Some of the processing steps shown in FIG. 7 may be interchanged without modifying the overall operation of the device. For the purposes of describing and defining the present invention it is noted that the terms "substantially" and "about" are utilized herein to represent the inherent degree of uncertainty that may be attributed to any quantitative comparison, value, measurement, or other representation. The terms "substantially" and "about" are utilized herein to represent the degree by which a quantitative representation may vary from a stated reference without resulting in a change in the basic function of the subject matter at issue.

It is also noted that recitations herein of "at least one" parameter, component, element, etc., should not be used to create an inference that the alternative use of the articles "a" or "an" should be limited to a single parameter, component, element, etc.

It is also noted that recitations herein of a component of the present disclosure being "configured" in a particular way, "configured" to embody a particular property, or function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

It is further noted that terms like "preferably," "generally," "commonly," "desirably", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Rather, the claims appended hereto should be taken as the sole representation of the breadth of the present disclosure and the corresponding scope of the various inventions described herein. Further, it will be apparent that modifications and variations are possible without departing from the scope of the invention defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A diabetes therapy device comprising:
   a profile memory, wherein the profile memory stores a parameter profile and a reference time mark,
      wherein the parameter profile is an insulin infusion rate profile which is pre-defined, cyclic, and defines the rate of insulin administration as a function of time for a generally circadian chronobiological cycle, the generally circadian chronobiological cycle having a length,
      wherein the beginning of the generally circadian chronobiological cycle sets the reference time mark and initializes a running time; and
   a controller unit and a going-to-bed sensor,
      wherein the controller unit is coupled to the profile memory and determines insulin amounts to be administered as a function of the running time in accordance with a current matching of the parameter profile and the running time,
      wherein the determined insulin amounts are based on the at least one parameter,
      wherein the controller unit modifies the current matching of the parameter profile and the running time, and
      wherein the controller unit:
         receives trigger information that is indicative of an upcoming cycle trigger event occurring at an upcoming trigger time,
            wherein the upcoming cycle trigger event is a defined event that generally occurs once per day and triggers the beginning of the generally circadian chronobiological cycle, wherein the upcoming cycle trigger event is the diabetic going to bed, falling asleep or waking up, and
            wherein the going-to-bed sensor is operatively coupled to the controller unit, and wherein the going-to-bed sensor detects at least one of the following actions: falling asleep, being asleep, waking up, getting up, and an auxiliary event, wherein the occurrence of the auxiliary event is correlated with falling asleep, being asleep, waking up, or getting up,
         computes a modified matching based on the reference time mark and the upcoming trigger time, wherein the modified matching is time-shifted from the current matching,
         applies the modified matching by making the modified matching the current matching, such that future insulin amounts to be administered are determined in accordance with the modified matching; and
         temporarily determines the insulin amounts to be administered in accordance with a transition profile when the controller applies the modified matching, wherein the transition profile provides a smooth transition in insulin amount to be administered when transitioning from the current matching to the modified matching.

2. The diabetes therapy device of claim 1, wherein the controller unit computes the modified matching such that the reference time mark is aligned with the upcoming trigger time.

3. The diabetes therapy device of claim 1, wherein the profile memory stores a standard matching of the parameter profile, and wherein the controller unit applies the standard matching by making the standard matching the current matching, such that the future insulin amounts to be determined with the standard matching.

4. The diabetes therapy device of claim 1, wherein the transition profile has a time span shorter than the length of the generally circadian chronobiological cycle.

5. The diabetes therapy device of claim 1, wherein the transition profile is either constant or is given by a section of the parameter profile stored by the profile memory.

6. The diabetes therapy device of claim 1, wherein controller unit temporarily blocks the application of the modified matching.

7. The diabetes therapy device according to claim 6, wherein the controller unit temporarily blocks applying the modified matching if a time difference of the upcoming trigger time to a last previous occurrence of the cycle trigger time is smaller than a minimum cycle interval.

8. The diabetes therapy device of claim 1, wherein the controller unit applies the modified matching without having received information indicative of a cycle trigger event.

9. The diabetes therapy device according to claim 8, wherein the controller unit receives information indicative of a further event, and wherein the controller unit applies the modified matching if the difference between a current point in time and a previous occurrence time of the further event exceeds a maximum awake interval without a cycle trigger event having occurred since the previous occurrence time of the further event.

10. The diabetes therapy device of claim 1, wherein the transition profile bridges a jump in the insulin amount to be administered between the current matching and the modified matching.

11. The diabetes therapy device of claim 1, wherein the transition profile bridges a gap formed when the parameter profile is shorter than the time between cycle trigger events.

12. A method of treating diabetes, the method comprising:
providing a profile memory, wherein the profile memory stores a parameter profile and a reference time mark,
wherein the parameter profile is an insulin infusion rate profile which is pre-defined, cyclic and defines the rate of insulin administration as a function of time for a generally circadian chronobiological cycle, the generally circadian chronobiological cycle having a length,
wherein the beginning of the generally circadian chronobiological cycle sets the reference time mark and initializes a running time; and
providing a controller unit and a going-to-bed sensor,
wherein the controller unit is coupled to the profile memory and determines insulin amounts to be administered as a function of the running time in accordance with a current matching of the parameter profile and the running time,
wherein the determined insulin amounts are based on the at least one parameter, and
wherein the controller unit modifies the current matching of the parameter profile and the running time;
receiving trigger information that is indicative of an upcoming cycle trigger event occurring at an upcoming trigger time,
wherein the upcoming cycle trigger event is a defined event that generally occurs once per day and triggers the beginning of the generally circadian chronobiological cycle
wherein the upcoming cycle trigger event the diabetic going to bed, falling asleep or waking up, and
wherein the going-to-bed sensor is operatively coupled to the controller unit, and wherein the going-to-bed sensor detects at least one of the following actions: falling asleep, being asleep, waking up, getting up, and an auxiliary event, wherein the occurrence of the auxiliary event is correlated with falling asleep, being asleep, waking up, or getting up;
computing a modified matching based on the reference time mark and the upcoming trigger time, wherein the modified matching is time-shifted from the current matching;
applying the modified matching by making the modified matching the current matching, such that future insulin amounts to be administered are determined in accordance with the modified matching; and
determining temporarily the insulin amounts to be administered in accordance with a transition profile when applying the modified matching, wherein the transition profile provides a smooth transition in insulin amounts to be administered when transitioning from the current matching to the modified matching.

13. The method of claim 12, wherein the transition profile has a time span shorter than the length of the generally circadian chronobiological cycle.

14. The method of claim 12, wherein the transition profile is either constant or is given by a section of the parameter profile stored by the profile memory.

15. The method of claim 12, wherein the transition profile bridges a jump in the insulin amount to be administered between the current matching and the modified matching.

16. The method of claim 12, wherein the transition profile bridges a gap formed when the parameter profile is shorter than the time between cycle trigger events.

* * * * *